(12) United States Patent
Flanagan

(10) Patent No.: US 7,828,767 B2
(45) Date of Patent: Nov. 9, 2010

(54) BALLOON DESIGN AND WELD DESIGN TO INCREASE EASE OF RE-WRAPPING AND DECREASE WITHDRAWAL FORCE

(75) Inventor: Aiden Flanagan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 37 days.

(21) Appl. No.: 12/129,380

(22) Filed: May 29, 2008

(65) Prior Publication Data
US 2009/0299283 A1     Dec. 3, 2009

(51) Int. Cl.
*A61M 37/00*     (2006.01)
(52) U.S. Cl. ................................. 604/103.08
(58) Field of Classification Search ........... 604/103, 604/103.08
See application file for complete search history.

(56) References Cited

U.S. PATENT DOCUMENTS

| 4,941,877 | A | | 7/1990 | Montano, Jr. | |
|---|---|---|---|---|---|
| 5,041,125 | A | | 8/1991 | Montano, Jr. | |
| 6,071,285 | A | * | 6/2000 | Lashinski et al. | 623/1.11 |
| 6,740,191 | B2 | * | 5/2004 | Clarke et al. | 156/272.8 |
| 7,419,563 | B2 | * | 9/2008 | Holman et al. | 156/272.2 |
| 2003/0163157 | A1 | * | 8/2003 | McMorrow et al. | 606/194 |
| 2005/0059989 | A1 | | 3/2005 | Eidenschinnk | |
| 2005/0251194 | A1 | | 11/2005 | McHale | |
| 2007/0167973 | A1 | * | 7/2007 | Stupecky et al. | 606/192 |

FOREIGN PATENT DOCUMENTS

| EP | 0730879 A1 | 2/1996 |
|---|---|---|
| WO | 2004101059 A1 | 11/2004 |

\* cited by examiner

*Primary Examiner*—Nicholas D Lucchesi
*Assistant Examiner*—Diva Ranade
(74) *Attorney, Agent, or Firm*—Vidas, Arrett & Steinkraus P.A.

(57) ABSTRACT

A balloon catheter that has at least one shaft, and a balloon. The balloon has a first weld region, a first cone region, a middle region, a second cone region and a second weld region where the first weld region engages the balloon to the at least one shaft, the first region is adjacent to the first weld region, the middle region is between the first cone region and the second cone region, the second cone region is adjacent to the second weld region, and the second weld region engages the balloon to at least one shaft. The balloon has an uninflated state and an inflated state, where the balloon has at least one fold extending from the first weld region to the second weld region in the uninflated state and the first and second cone regions of the balloon have at least one fold in the inflated state.

17 Claims, 10 Drawing Sheets

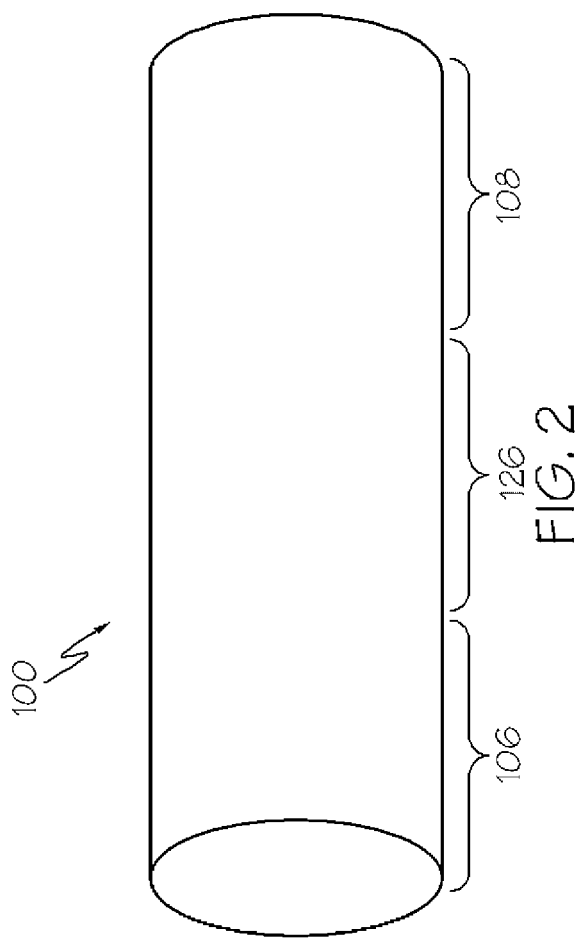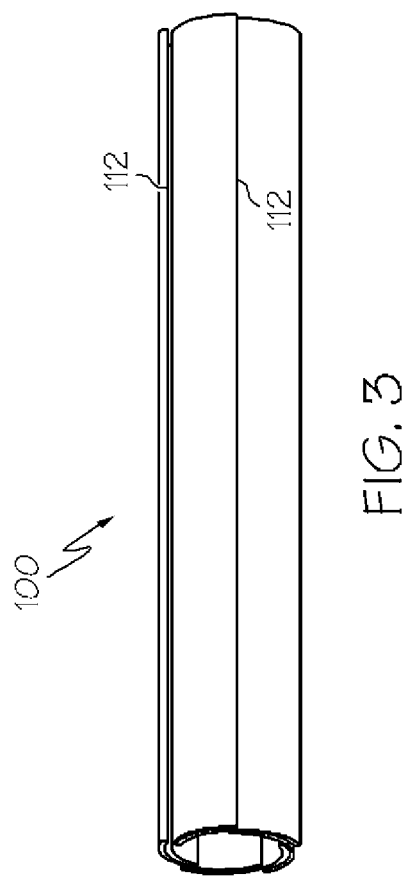

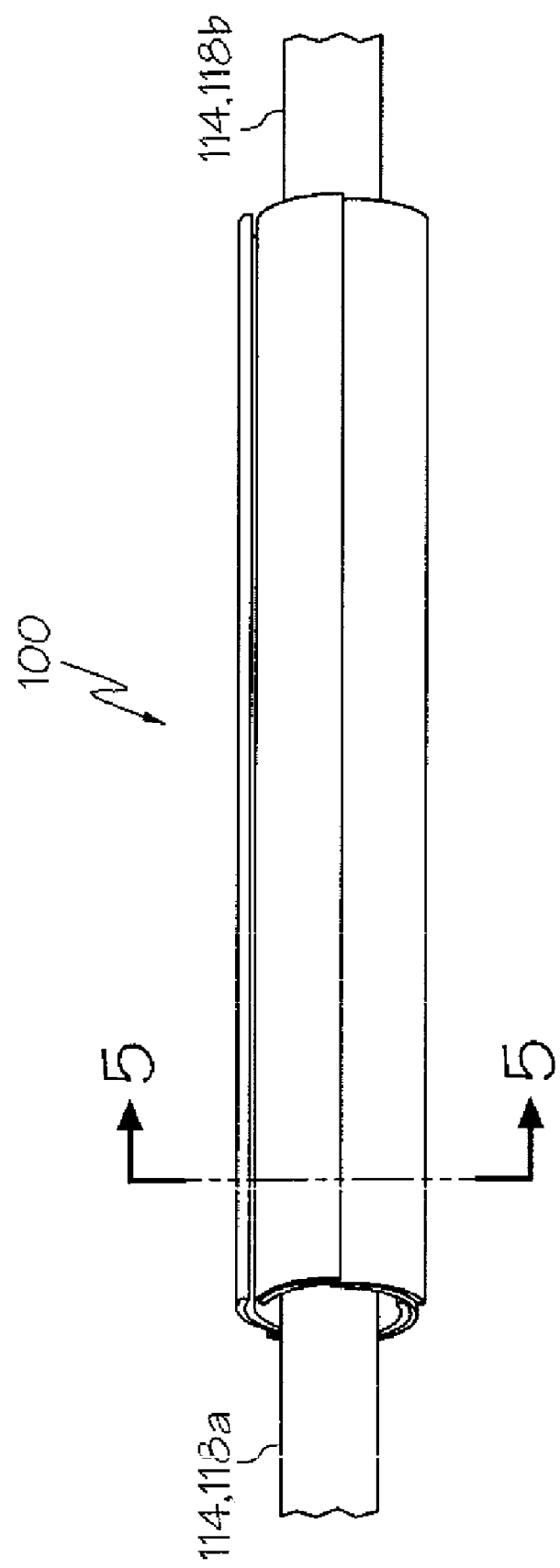

BALLOON DESIGN AND WELD DESIGN TO INCREASE EASE OF RE-WRAPPING AND DECREASE WITHDRAWAL FORCE

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments this invention relates to a balloon catheter with a balloon having folds or pleats that has been welded to at least one shaft, outer and/or inner, of the balloon catheter. The invention is also directed to methods of making a balloon catheter with a balloon having folds or pleats that has been welded to at least one shaft, outer and/or inner, of the balloon catheter.

BACKGROUND OF THE INVENTION

Medical catheters having a balloon mounted thereon are useful in a variety of medical procedures. Balloon catheters may be used to widen a vessel into which the catheter is inserted by dilating the blocked vessel, such as in an angioplasty procedure. Balloon catheters may also be used to expand and/or seat a medical device such as a stent or graft at a desired position within a body lumen. In all of these applications, fluid under pressure may be supplied to the balloon through an inflation lumen in the catheter, thereby expanding the balloon.

It is essential in the manufacture of balloon catheters to properly seal the balloon to the catheter, e.g. by welding. The seal must be able to withstand the high pressures to which it is subjected on inflation of the balloon. A poor seal may result in leakage of inflation fluid and inability to achieve the desired pressure or even rapid loss of pressure and deflation of the balloon. In addition, it is desirable to shape the outside surface of the weld region to provide a smooth transition from the outer shaft to the balloon.

FIG. 1 is an end view of a PRIOR ART balloon catheter 22. Known balloon catheters 22, such as the example shown in FIG. 1, have a preformed balloon 10 which has a center region 26, proximal and distal cones 4, and proximal and distal waists. The waists of the balloon are welded 20 onto the shafts of the catheter 22. The cone 4 of the balloon 10 has a smooth surface and a large outer diameter at one end and a smaller outer diameter at the other end with increasing thickness as the outer diameter of the cone 4 is reduced. As shown in FIG. 1, the center region of the balloon 10 is folded to a small outer diameter but the proximal and distal cones 4 are not folded. This is due to the fact that the balloon 10 is folded after it has been welded onto the shafts 18 of the balloon catheter 22. Thus, there is a relatively bulky transition region between the center region 26 of the balloon 10 and the cone 4 that has an increased outer diameter. This relatively bulky transition region is caused by several factors which include bunching due to the fact that the folding does not end sharply and the increased thickness as the outer diameter of the cone 4 is reduced, as shown in FIG. 1.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1 56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a balloon catheter where a balloon cylinder is folded to form pleats and then is welded directly to the catheter. The proximal portion of the balloon is welded to the outer shaft of the balloon catheter and the distal portion of the balloon is welded to the inner shaft of the balloon catheter. The invention is also directed to making a balloon catheter with a folded/pleated balloon welded to the balloon catheter.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 2 is a side view of a balloon cylinder.

FIG. 3 is the balloon cylinder of FIG. 2 folded.

FIG. 4 is a side view of the folded balloon cylinder of FIG. 3 disposed about a catheter shaft which is disposed about a mandrel.

DETAILED DESCRIPTION OF THE INVENTION

Figure 1:
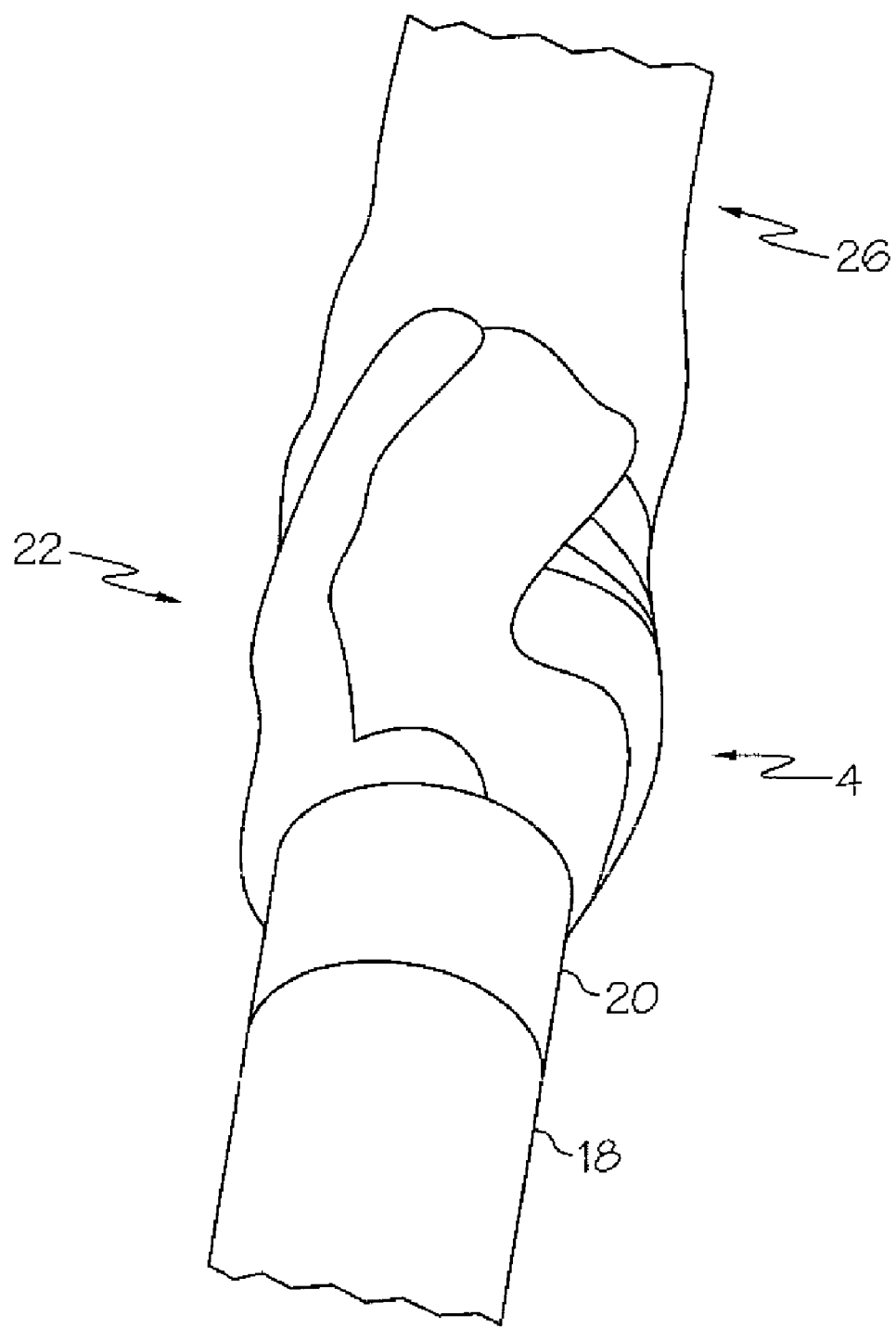
FIG. 1 is an end view of a PRIOR ART balloon catheter.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The invention is directed to a balloon catheter 122 with a balloon 100 that has folds or pleats 112 extending from a first end of the balloon 100 to a second end of the balloon, and that has been welded to at least one shaft 118, outer and/or inner, of the balloon catheter 122. The invention is also directed to methods of making a balloon catheter 122 with a balloon 100 having folds or pleats 112 that has been welded to at least one shaft 118, outer and/or inner, of the balloon catheter 122. As used in this application, shaft 118 includes both the outer shaft 118a and/or the inner shaft 118b of a balloon catheter 122. In at least one embodiment, the proximal end region 106 of a balloon 100 with pleats 112 is engaged to the outer shaft 118a of a balloon catheter 122 and the distal end region 108 of the balloon 100 is engaged to the inner shaft 118b of the balloon catheter 122, where the inner shaft 118b extends distally from the distal end of the outer shaft 118a, as is known in the art.

Figure 11:
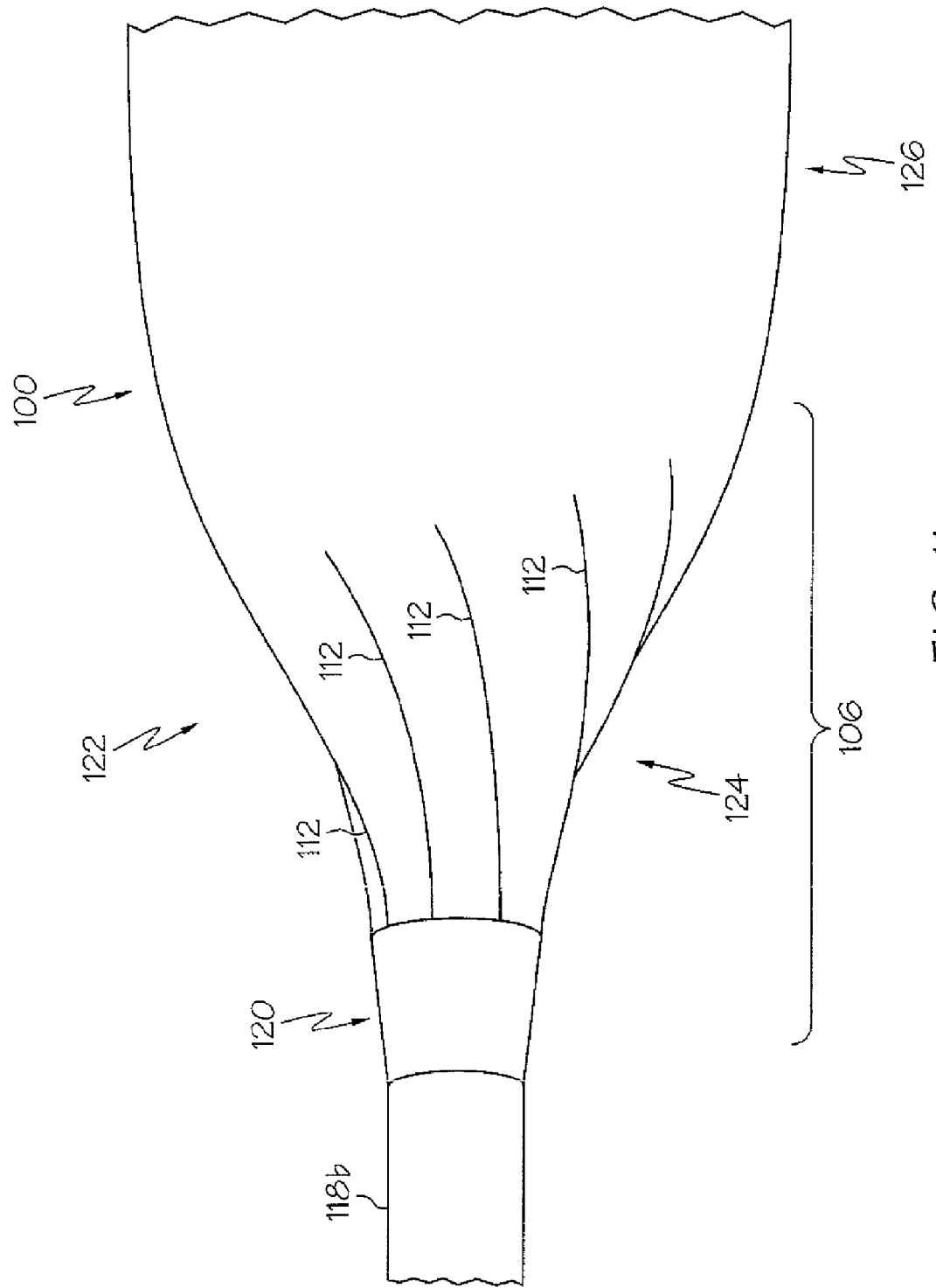
FIG. 11 is a side view of the balloon catheter in FIG. 9 with the balloon in an inflated state.

The manufacture of the inventive balloon catheter 122 begins with a balloon cylinder 100, as shown in FIG. 2. The balloon cylinder 100 has a proximal end region 106, a middle region 126 and a distal end region 108. The proximal end region 106 includes a weld region 120 and a cone region 124, as shown in FIG. 11. Similarly, the distal end region 108 includes a weld region 120 and a cone region 124. Each of the regions 106,124,108,120,126 has any longitudinal length.

The balloon cylinder 100 is folded to form folds or pleats 112. In some embodiments, the folds 112 extend along the entire longitudinal length of the balloon cylinder 100, i.e. from a first end of the balloon cylinder 100 to a second end of the balloon cylinder 100, as shown in FIG. 3. In other embodiments, the folds 112 are incorporated into the proximal and distal end regions 106,108 of the balloon cylinder 100 while the middle region 126 of the balloon cylinder 100 has no folds 112. In at least one embodiment, the folds 112 are parallel to the longitudinal axis of the balloon cylinder 100. In other embodiments, the folds 112 are at an oblique angle to the longitudinal axis of the balloon cylinder 100. An oblique angle, as used in this application, is an angle between 0 and 180 degrees and includes 90 degrees.

In some embodiments, the balloon cylinder 100 is disposed about the catheter shaft(s) 118 of the balloon catheter 122, which is disposed about a mandrel 114, then folds 112 are incorporated into the balloon cylinder 100 and then the folded balloon cylinder 100 is welded to the catheter shaft(s) 118. In other embodiments, the balloon cylinder 100 is disposed about a mandrel 114, folds 112 are incorporated into the balloon cylinder 100, the mandrel 114 is removed and replaced with the catheter shaft(s) 118 of the balloon catheter 122 so that the folded balloon cylinder 100 is disposed about the catheter shaft(s) 118 and then the folded balloon cylinder 100 is welded to the catheter shaft(s) 118. FIG. 4 shows the folded balloon cylinder 100 disposed about a catheter shaft(s) 118 which is disposed about a mandrel 114.

Any method can be used to fold the balloon cylinder 100, even methods used to fold the balloon 100 after it has been welded to the catheter shaft(s) 118 of the balloon catheter 122. As used in this application, the term "fold" includes pleats, wings, and any similar structure. Non-limiting examples of methods of balloon folding are discussed in commonly Assigned U.S. Patent Application Publication No. 2003/0163157, entitled Balloon Folding Apparatus, Methods and Products and U.S. Patent Application Publication No. 2005/0251194, entitled Curved Wing Balloon and Manufacture Thereof, each of which are hereby incorporated by reference in their entirety.

Figure 5:
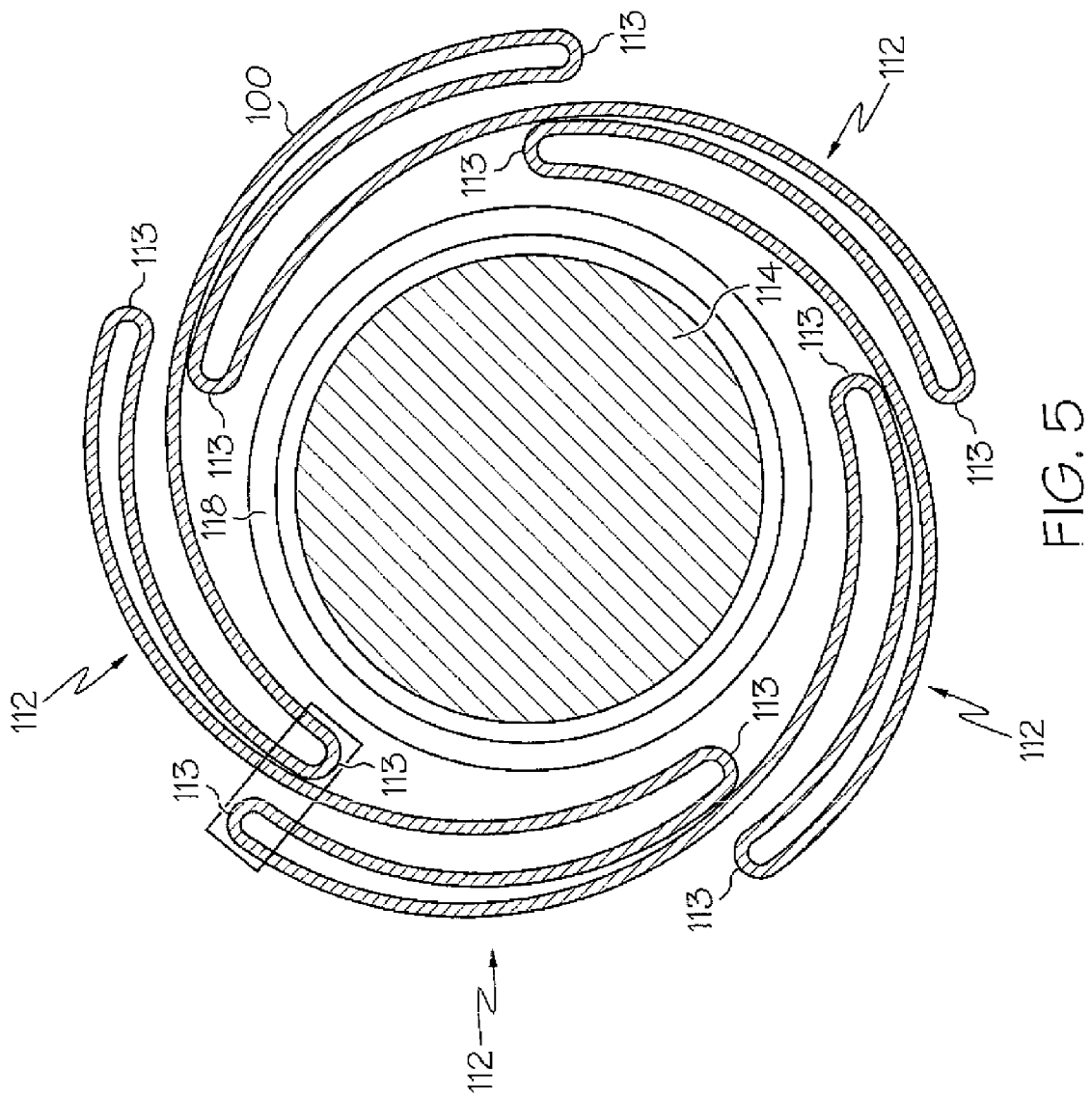
FIG. 5 is a cross-sectional view of FIG. 4 taken at line 5-5 showing a fold overlap embodiment.
Figure 6:
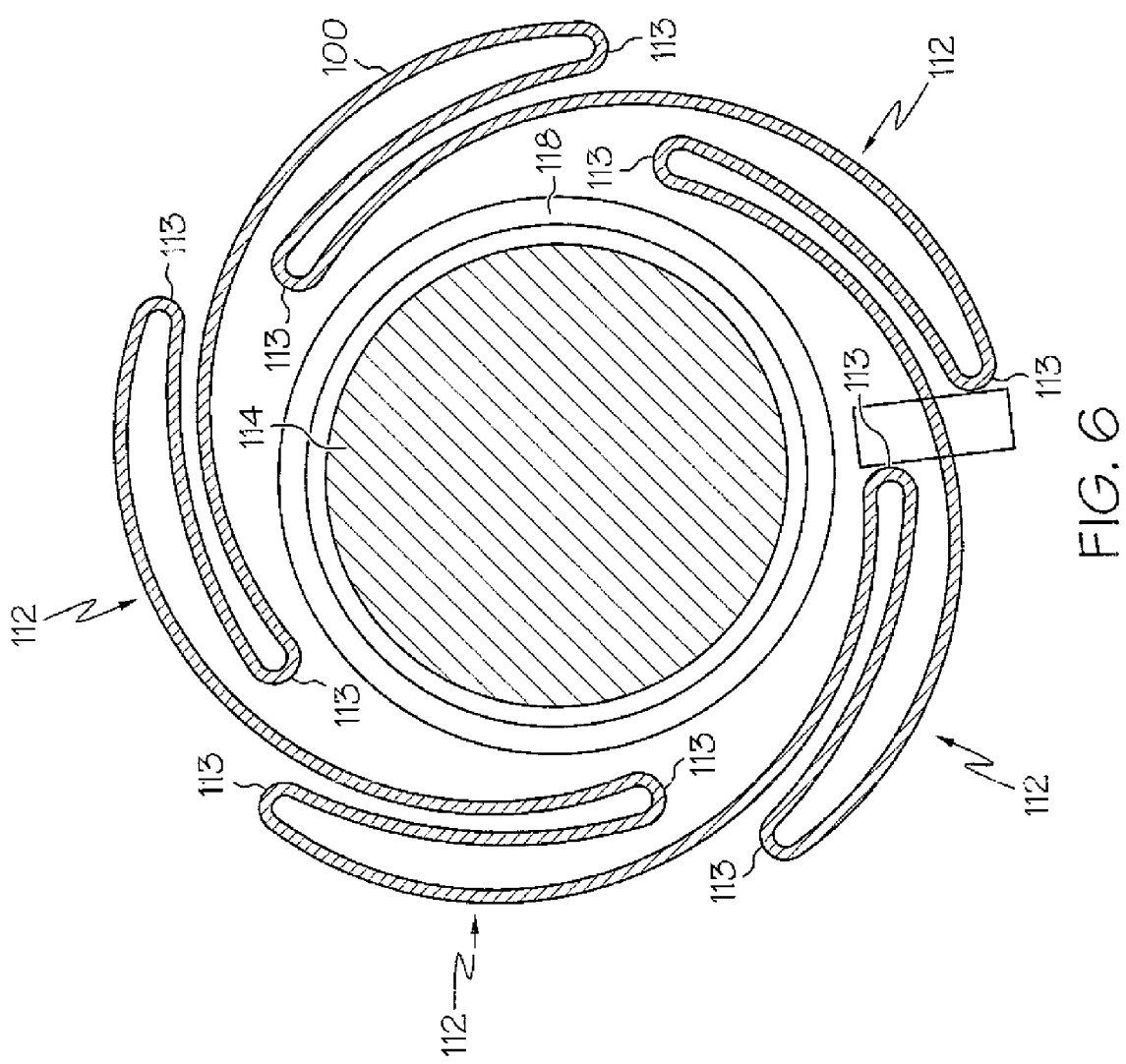
FIG. 6 is a cross-sectional view of FIG. 4 taken at line 5-5 with another fold overlap embodiment.

FIGS. 5 and 6 are cross-sectional views taken at line 5-5 of FIG. 4 of the proximal end region 106 of the balloon cylinder 100 after it has been folded. Note that a cross-sectional view of the distal end region 108 of the balloon cylinder 100 after it has been folded would have the same configuration. The balloon cylinder 100 is disposed about the shaft(s) 118 of the balloon catheter 122 which is disposed about mandrel 114. FIGS. 5 and 6 show two non-limiting examples of the placement of the folds 112 formed in the balloon cylinder 100. In at least one embodiment, the ends 113 of radially adjacent folds 112 are overlapping, as indicated by the box in FIG. 5 that surrounds one set of overlapping ends 113. It is within the scope of the invention for there to be any amount of overlap of the ends 113. In some embodiments, the ends 113 overlap one another for the same distance. In other embodiments, the ends 113 overlap one another for different distances. In at least one embodiment, the ends 113 of radially adjacent folds 112 do not overlap, as shown by the box in FIG. 6 which is between the ends 113. It is within the scope of the invention for any distance to separate the ends 113 of the folds 112. In some embodiments, the ends 113 are separated from one another by the same distance. In other embodiments, the ends 113 are separated from one another by different distances.

Figure 7:
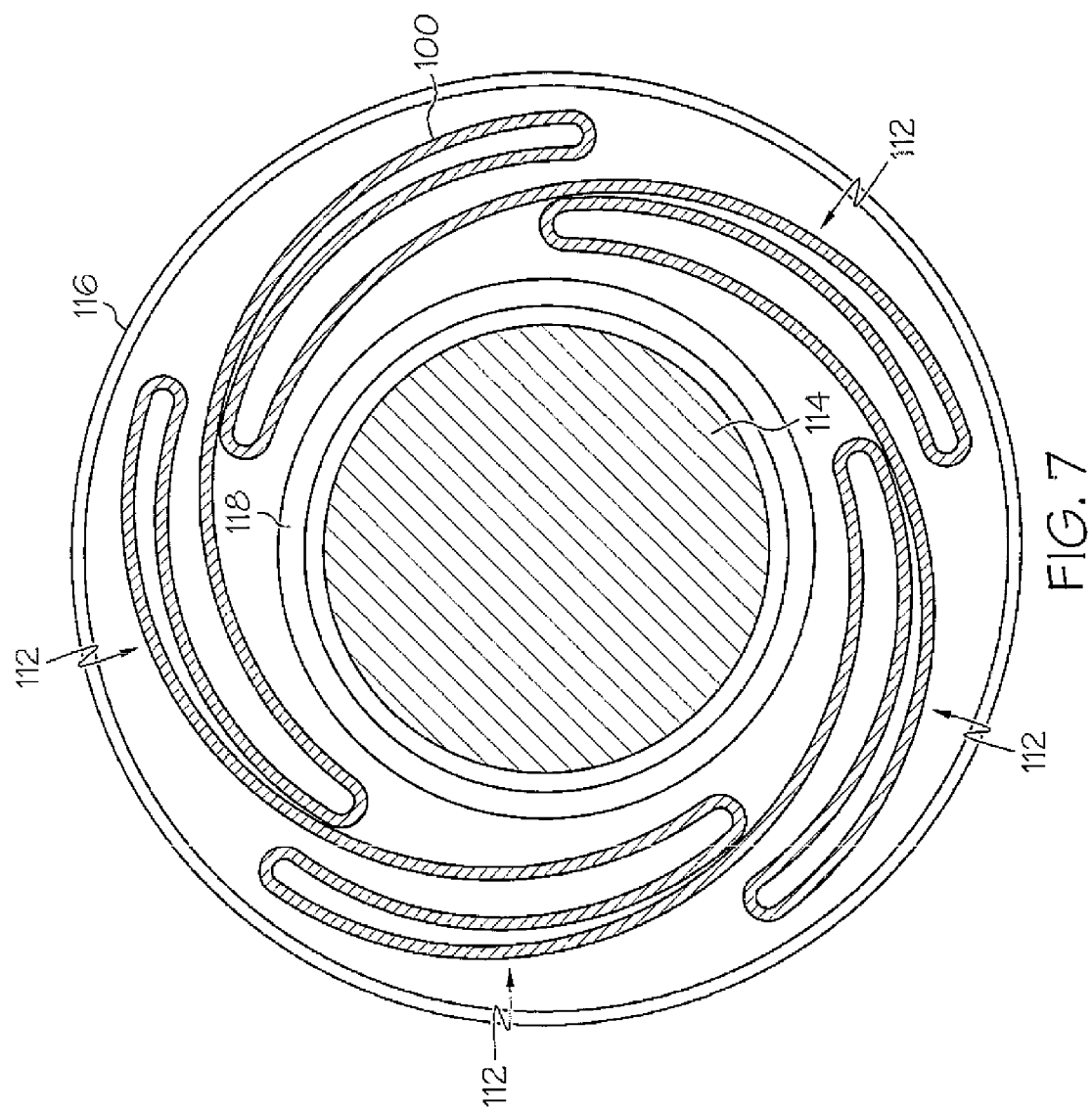
FIG. 7 is the cross-sectional view of FIG. 5 with heatshrink surrounding the folded balloon at the weld region.

In some embodiments, at least one section of heat shrink material 116 is disposed about the balloon cylinder 100 after the balloon cylinder 100 is folded. In other embodiments, at least one section of heat shrink material 116 is placed about the balloon cylinder 100 before the balloon cylinder 100 is folded. FIG. 7 shows a section of heat shrink material 116 disposed about the folded balloon cylinder 100, which is disposed about catheter shaft(s) 118 that is disposed about mandrel 114. In some embodiments, the section(s) of heat shrink material 116 is heated so that the heat shrink material 116 shrinks and provides a force against the weld region 120 that presses the folds 112 of the folded balloon cylinder 100 radially inward, which eliminates air pockets in the folds 112 of the balloon 100.

The heat shrink material 116 has any length. In some embodiments, one section of heat shrink material 116 that has a length equal to the length of the balloon cylinder 100 is used. In other embodiments, two sections of heat shrink material 116 are used, with one section of heat shrink material 116 being placed over the proximal weld region 120 and the second section of heat shrink material 116 being disposed about the distal weld region 120. Any suitable heat shrink material 116 may be used. Examples of suitable heat shrink material 116 which may be used, include but are not limited to, polyethylene (e.g. polyolefin), RNF-100 which is a heat shrink tubing available from Raychem Corporation, Kynar™, nylon, polyvinalchloride, polytetrafluoroethylene and fluorinated ethylene polymer (FEP).

The folded balloon cylinder 100 is welded to the catheter shaft(s) 118 of a catheter to form a balloon catheter 122. Thus, in at least one embodiment, there are two weld regions 120, a proximal weld region 120 at the proximal end region 106 of the balloon cylinder 100 and a distal weld region 120 at the distal end region 108 of the balloon cylinder 100. In each weld region 120, the folds 112 of the balloon cylinder 100, are welded directly to shaft(s) 118 of the balloon catheter 122 so that the balloon 100 does not have a waist. In some embodiments, the balloon 100 has a low profile.

Welds 120 are formed by any mechanism desired, for example, but not limited to, through transmission laser welding and direct or indirect application of heat to the weld site by any conventional method. In some embodiments, welds are formed using a laser, e.g. a $CO_2$ laser or a diode laser. Examples of different weld 120 configurations and methods which may be used to weld the balloon wings 112 to the shaft(s) 118 are discussed in commonly assigned U.S. Application Publication No. 2008/0077173 entitled Designs for Balloon Welds, hereby incorporated by reference in its entirety.

Figure 8:
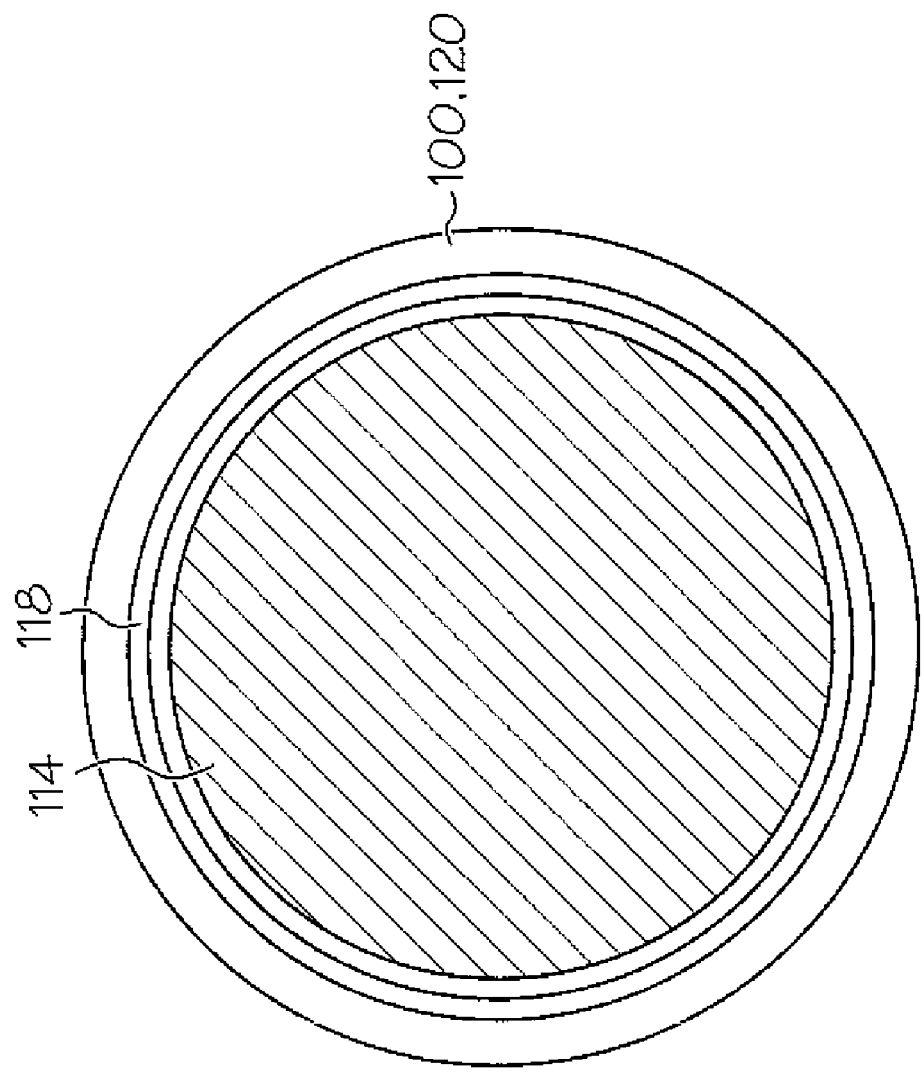
FIG. 8 is the cross-sectional view of FIG. 7 after the weld has been formed.

If at least one section of heat shrink material 116 has been disposed about the balloon cylinder 100, the heat from the laser further shrinks the heat shrink material 116, thereby squeezing the molten polymer layers together, as shown in FIG. 8. In some embodiments, the at least one section of heat shrink material 116 is removed from the balloon cylinder 100 after the balloon cylinder 100 has been welded to catheter shaft(s) 118. In at least one embodiment, the weld 120 has even material thickness. In one embodiment, even material thickness of the weld 120 is obtained when the ends of the folds/pleats 112 do not overlap but have minimal separation, as shown for example, in FIG. 6. As discussed in U.S. Application Publication No. 2008/0077173, flexibility of the weld 120 can vary. In some embodiments, welding the balloon wings 100 to shaft(s) 118 increases the flexibility of the weld 120.

Figure 9:
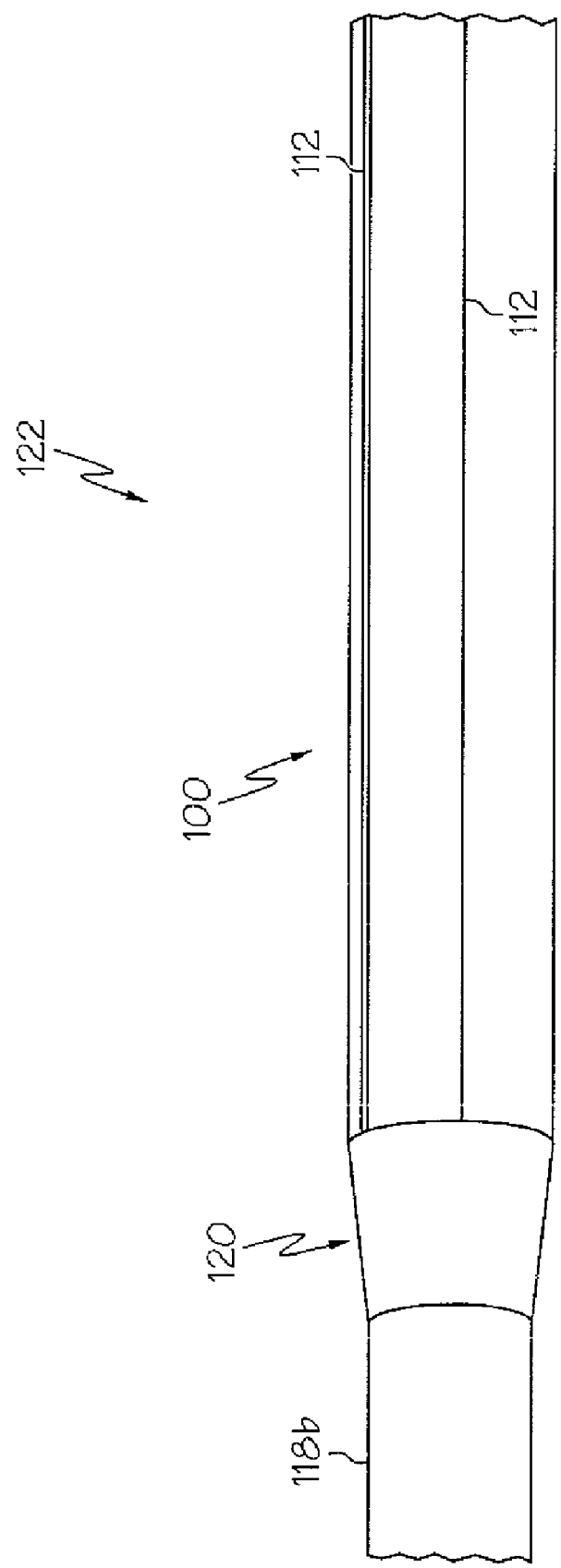
FIG. 9 is a side view of the balloon catheter after the balloon has been welded to the catheter, with the balloon in a deflated state.
Figure 10:
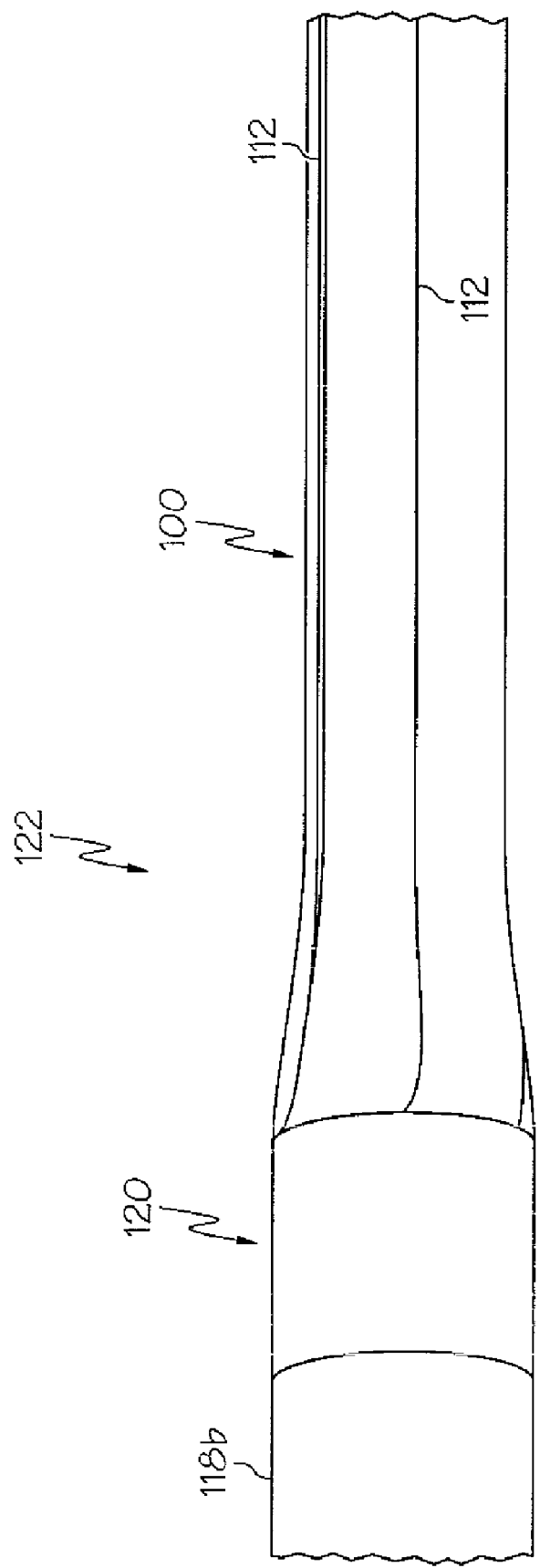
FIG. 10 is a side view of the balloon catheter after the balloon has been welded to the catheter with a larger diameter proximal shaft, with the balloon in a deflated state.

FIGS. 9-11 are side views of the balloon catheter 122 with the balloon 100 in different states of expansion. The balloon 100 is in an unexpanded state in FIGS. 9 and 10, and in an inflated or expanded state in FIG. 11. FIG. 10 shows a balloon 100 that has been welded to an outer shaft 118a of the balloon catheter 122 that has a larger diameter than the inner shaft 118b of the balloon catheter 122 (note that the inner shaft 118b is not shown in FIG. 10). In at least one embodiment, the balloon 100 has a smooth middle region 126 and pleated cone regions 124 when the balloon 100 is inflated, as shown in FIG. 11. In some embodiments, the folds 112 of the pleated cone regions 124 facilitate re-wrapping along the original folds 112. In at least one embodiment, the balloon 100 can be "cone puffed." Cone puffing is the slight inflation of the balloon 100 after a stent has been crimped onto the balloon 100 while the stent is restrained to prevent expansion of the stent and is used to prevent slippage or movement of the stent.

Polymeric materials that may be used for the shafts of balloon catheters include, but are not limited to, high density polyethylene (HDPE), polyamides, the polyetheramide copolymer family, HDPE with and without compatibilizers, low density polyethylene (LDPE), LDPE with and without compatibilizers, linear low density polyethylene (LLDPE), LLDPE with and without compatibilizers, polyethylene copolymers such as ethylene vinyl acetate copolymer (EVA) and other vinyl acetates, urethanes, polybutylene terephthalate (PBT), thermoplastic elastomers, isonomers, ethylene acrylic acid polymers, polyether block amide, and ethylene acrylic acid copolymer (EAA), polyurethane, polyesters such as polyethylene terephthalate (PEI), polybutylene terephthalate (PBT), copolyesters such as Hytrel, other thermoplastic elastomers such as thermoplastic polyolefin (IPO), styrenic thermoplastic elastomers such as C-Flex, and ionomers such as Surlyn and any combination thereof.

Polymer materials that can be used for balloons 10 include, but are not limited to, ethylene-vinyl acetate, polyvinyl chloride (PVC), olefin copolymers or homopolymers, polyethylenes, polyurethanes, crosslinked low density polyethylenes (PEIs), highly irradiated linear low density polyethylene (LDPE), acrylonitrile polymers and copolymers, acrylonitrile blends and ionomer resins, polyethylene terephthalates, polyacrylenesulfide, and copolyesters, nylon, and polyamines. Other balloon materials may also be used.

In some embodiments the balloon catheter may include one or more areas, bands, coatings, members, etc. that is (are) detectable by imaging modalities such as X-Ray, MRI, ultrasound, etc. In some embodiments at least a portion of the balloon catheter is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A balloon catheter, the balloon catheter comprising:
at least one shaft; and
a balloon, the balloon comprising a first weld region, a first cone region, a middle region, a second cone region and a second weld region, the first weld region engaging the balloon to the at least one shaft, the first cone region adjacent to the first weld region, the middle region between the first cone region and the second cone region, the second cone region adjacent to the second weld region, the second weld region engaging the balloon to the at least one shaft, the balloon having an uninflated state and an inflated state, the balloon having at least one fold extending from the first weld region to the second weld region in the uninflated state and the first and second cone regions of the balloon having at least one fold in the fully inflated state.

2. The balloon catheter of claim 1, the at least one shaft comprising an outer shaft and an inner shaft, the first weld region engaging the balloon to a portion of the outer shaft and the second weld region engaging the balloon to a portion of the inner shaft.

3. The balloon catheter of claim 1, the at least one fold being a plurality of folds, each of the plurality of folds having a first end and a second end, radially adjacent ends being overlapping.

4. The balloon catheter of claim 1, the at least one fold being a plurality of folds, the plurality of folds having even material thickness.

5. A method for making a balloon catheter comprising:
providing a balloon cylinder, the balloon cylinder having a first end and a second end, the first end and the second end separated by a longitudinal length;
providing a catheter comprising at least one shaft;
incorporating at least one fold, the at least one fold extending from the first end to the second end of the balloon cylinder; and
welding the balloon cylinder with the at least one fold to the at least one shaft of the catheter.

6. The method of claim 5, wherein a laser is used to weld the balloon cylinder to the catheter.

7. The method of claim 5, the at least one fold being a plurality of folds, each of the plurality of folds having a first end and a second end, radially adjacent ends being overlapping.

8. The method of claim 5, the at least one fold being a plurality of folds, the plurality of folds having even material thickness.

9. The method of claim 5, wherein the balloon cylinder is disposed about the at least one shaft when incorporating the at least one fold.

10. The method of claim 9, further comprising providing a mandrel, the balloon cylinder being disposed about the at least one shaft which is disposed about the mandrel when incorporating the at least one fold.

11. The method of claim 10, wherein the balloon cylinder is disposed about the at least one shaft which is disposed about the mandrel when the balloon cylinder is welded to the at least one shaft of the catheter.

12. The method of claim 5, further comprising providing a mandrel, the balloon cylinder being disposed about the mandrel while incorporating the at least one fold.

13. The method of claim 12, further comprising removing the mandrel from within the balloon cylinder with at least one fold before welding the balloon cylinder with at least one fold to the at least one shaft.

14. The method of claim 5, further comprising
providing at least one section of heat shrink material;
disposing the at least one section of heat shrink material about at least a portion of the balloon cylinder; and
pre-shrinking the section of heat shrink material.

15. The method of claim 14, the at least one section of heat material having a length at least equal to the longitudinal length of the balloon cylinder.

16. The method of claim 14, the at least one section of heat shrink material comprising a first section and a second section, the balloon cylinder comprising a first weld region and a second weld region, the first section of heat shrink material being disposed about the first weld region and the second section of heat shrink material being disposed about the second weld region.

17. The method of claim 14, wherein pre-shrinking the section of heat shrink material presses the balloon cylinder onto the at least one shaft of the catheter.

* * * * *